United States Patent [19]

Matsumoto et al.

[11] Patent Number: 5,051,441

[45] Date of Patent: Sep. 24, 1991

[54] IMIDAZOLINE DERIVATIVE

[75] Inventors: Kazuo Matsumoto, Ibaraki; Mamoru Suzuki, Toyonaka; Kozo Yamamoto, Takatsuki; Isao Takata, Toyono; Yoshio Iwasawa, Toyonaka, all of Japan

[73] Assignee: Tanabe Seiyaku Co., Ltd., Osaka, Japan

[21] Appl. No.: 417,199

[22] Filed: Oct. 4, 1989

[30] Foreign Application Priority Data

Oct. 6, 1988 [JP] Japan .................. 63-253391

[51] Int. Cl.$^5$ .................. C07D 233/20; A61K 31/415
[52] U.S. Cl. .................... 514/401; 548/353
[58] Field of Search ............... 514/401, 341; 548/353; 546/278

[56] References Cited

U.S. PATENT DOCUMENTS 3,707,475 12/1972 Lombardino .................. 260/309
3,772,441 11/1973 Lombardino .................. 424/273
4,424,229 1/1984 Jorgensen et al. ............. 424/273

FOREIGN PATENT DOCUMENTS 0005219 4/1979 European Pat. Off.
0077024 8/1982 European Pat. Off.
0024629 8/1990 European Pat. Off.
10379 5/1972 Japan.
44279 1/1968 Switzerland.
454154 6/1968 Switzerland.

OTHER PUBLICATIONS

B. Karaman et al., Croatica Chemica Acta, No. 45 (1973), pp. 519-522.

Merck Index, 9th Edition, p. 51 (1976).
Kannar et al., Croatica Chemica Acta 45 (1973), pp. 519-522.
Hunter et al., Canadian Journal of Chemistry, vol. 50 (1972), pp. 669-677.
Zupanc et al., Bull. Soc. Chem. & Technolog., Sarajevo (Yugoslavia), 27/28 (1980-1981), pp. 71-80.

Primary Examiner—John M. Ford
Attorney, Agent, or Firm—Birch, Stewart, Kolasch & Birch

[57] ABSTRACT

Imidazoline derivative of the formula:

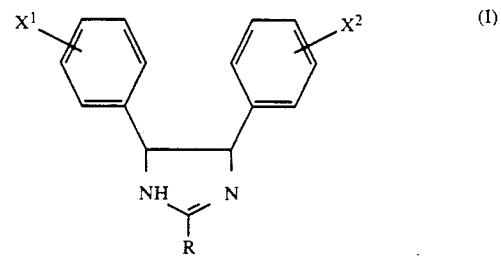

wherein R is a halogenophenyl group or a pyridyl group and $X^1$ and $X^2$ are a hydrogen atom or a lower alkoxy group, or a pharmaceutically acceptable salt thereof, which is useful as an immunomodulator and as an agent for the treatment and/or prophylaxis of rheumathoid arthritis, multiple sclerosis, systemic lupus erythemathodes, rheumatic fever and the like, a process for the preparation thereof, and a pharmaceutical composition containing said compound as an active ingredient.

4 Claims, No Drawings

IMIDAZOLINE DERIVATIVE

FIELD OF THE INVENTION

This invention relates to novel imidazoline derivatives and a process for the preparation thereof.

BACKGROUND OF THE INVENTION 2,4,5-Triphenyl-, 2,4,5-tris(4-chlorophenyl)-and 2,4,5-tris(4-methylphenyl)-derivatives of imidazoline are known [Merck Index 9, 51, Chroachica Chemica Acta, 45, 519 (1973) and Canadian Journal of Chemistry 50, 669 (1972)]. Among them, the 2,4,5-triphenylderivative is known to show cardiac inhibitory effect, but there have been known no pharmacological effect of the other two derivatives.

SUMMARY OF THE INVENTION

As a result of various investigations, it has been found that, while the above known compounds have the same substituents at 2-, 4-and 5-positions on the imidazoline ring, a group of imidazoline derivatives having different substituents between 2-position and 4-and 5-positions on the imidazoline ring are useful as an immunomodulator.

Thus, the objects of the invention are to provide novel imidazoline derivatives and a pharmaceutical composition containing the same. Another object of the invention is to provide a process for preparing said compounds. These and other objects and advantages of the invention will be apparent to those skilled in the art from the following description.

DETAILED DESCRIPTION OF THE INVENTION

This invention relates to imidazoline derivatives of the formula:

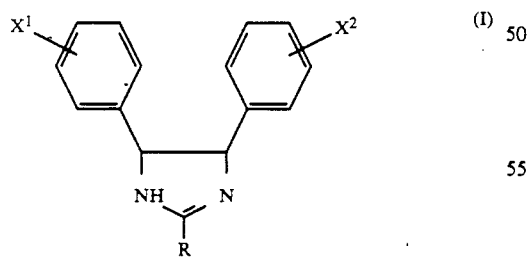

wherein R is a halogenophenyl group or a pyridyl group, and $X^1$ and $X^2$ are a hydrogen atom or a lower alkoxy group, or a pharmaceutically acceptable salt thereof.

The compound (I) of the invention or a salt thereof has a variety of excellent characteristics as an immunomodulator. For example, the compound (I) or a salt thereof shows potent macrophage migration enhancement activity in a macrophage migration assay which is used in measurement of cell-mediated immune activity. The imidazoline derivative (I) of the invention also shows such a potent immunomodulatory effect that a suppressed immune activity is raised and an augmented one is lowered to restore to a normal level. Further, the imidazoline derivative (I) or a pharmaceutically acceptable salt thereof has low toxicity and shows high safety.

Pharmaceutically preferred examples of the imidazoline derivative of the invention are those of the formula (I) wherein R is a halogenophenyl group and $X^1$ and $X^2$ are hydrogen atoms.

The imidazoline derivative (I) of the invention may exist in the form of stereoisomers due to two asymmetric carbon atoms and two tautomeric isomers shown in the formula:

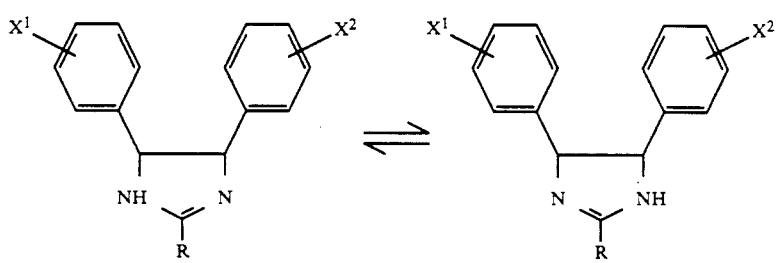

wherein R, $X^1$ and $X^2$ are the same as defined above, and this invention includes these isomers and a mixture thereof. Among cis- and trans- isomers of the imidazoline derivative (I) of the invention, cis- isomers are more preferred for pharmaceutical use.

According to the invention, the imidazoline derivative (I) can be prepared by condensing a compound of the formula:

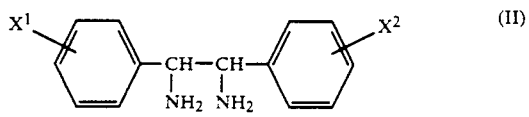

wherein $X^1$ and $X^2$ are the same as defined above, or a salt thereof and a compound of the formula:

wherein R is the same as defined above and $R^1$ is a lower alkyl group, or a salt thereof.

The condensation reaction proceeds in the presence or absence of a base in a solvent. The base includes alkali metal alkoxides, alkali metal hydroxides, alkali metal carbonates, alkali metal hydrogen carbonates, tri(lower alkyl)amines and the like. Examples of the salt of the starting compound (II) and (III) are conventional inorganic or organic acid addition salts. A lower alkanol, dioxane, tetrahydrofuran, dimethylformamide, dimethylsulfoxide and the like can be used as a solvent. The reaction is preferably carried out at a temperature of 0° to 100° C.

In this invention, a cis imidazoline derivative (I) can be obtained when an erythro compound is used as the starting material (II). On the other hand, a trans imidazoline derivative (I) can be obtained from a threo type starting material (II), and an optically active compound (I) can be obtained from an optically active starting material (II), respectively.

As mentioned hereinbefore, the compound (I) of the invention or a salt thereof shows a potent immunomodulatory effect. Especially, the compound (I) activates the migration of macrophage (i.e., the macropharge staying in a chronic inflammatory part) to allow it to leave the inflammatory part, and at the same time, the compound (I) allows the suppressive T-cell level to be restored. Therefore, the compound (I) is useful for the treatment and/or prophylaxis of rheumatoid arthritis, multiple sclerosis, systemic lupus, erythematodes, rheumatic fever and the like.

The imidazoline derivative (I) of the invention can be used for pharmaceutical use either in the form of a free base or a salt. Pharmaceutically acceptable salts of the compound (I) include, for example, inorganic acid addition salts such as hydrochloride, hydrobromide, phosphate and sulfate, and organic acid addition salts such as oxalate, acetate, lactate, citrate, tartarate, fumalate, maleate, aspartate, methanesulfonate and benzoate.

The imidazoline derivative (I) or a salt thereof may be administered either orally or parenterally to a warm-blooded animal, including human beings, and may also be used in the form of a pharmaceutical preparation containing the same compound in admixture with pharmaceutical excipients suitable for oral or parenteral administration. The pharmaceutical preparations may be in solid form such as tablets, granules, capsules and powders, or in liquid form such as solutions, suspensions or emulsions. Moreover, when administered parenterally, it may be used in the form of injections.

The dose of the imidazoline derivative (I) or a salt thereof may vary depending on the route of administration, age, weight and condition of the patient and a kind of disease, and is preferably about 0.01 to 50 mg/kg a day, especially 0.1 to 10 mg/kg a day.

EXPERIMENT 1

Effect on alveolar macrophage migration

Japanese white female rabbits, weighing between 3 and 4 kg, were sacrificed under anesthesia. Alveolar macrophages were obtained by pulmonary lavage with saline. In a "test group", the macrophages were migrated in the RPMI-1640 medium containing 5% rabbit serum and $10^{-7}$ or $10^{-9}$ M of a test compound. Said migration test was carried out at 37° C. for 24 hours according to the method described in Journal of Leukocyte Biology 42: 197–203 (1987). The resulting migration was projected at about 15 times magnification and traced. Then, the migration area was measured with a planimeter.

The migration of macropharges in a "positive control group" was measured by the use of the RPMI-1640 medium containing 5% rabbit serum and 5 mM of L-fucose, instead of the medium containing the test compound. On the other hand, in a "control group", the experiment was carried out by the use of a medium containing 5% rabbit serum only. The migration index was calculated by the following formula:

Migration Index =

$$\frac{\left(\begin{array}{c}\text{migration area of}\\\text{test group}\end{array}\right) - \left(\begin{array}{c}\text{migration area of}\\\text{control group}\end{array}\right)}{\left(\begin{array}{c}\text{migration area of}\\\text{positive control group}\end{array}\right) - \left(\begin{array}{c}\text{migration area of}\\\text{control group}\end{array}\right)} \times 100$$

The results are shown in Table 1.

TABLE 1

| | Effect on alveolar macrophage migration | |
|---|---|---|
| | Migration index | |
| Test Compounds | $10^{-9}$ (M) | $10^{-7}$ (M) |
| (the compound of the present invention) Cis-2-(4-chlorophenyl)-4,5-diphenyl-2-imidazoline hydrochloride | 113.9 | 142.5 |
| (Known compound) Cis-2,4,5-tris(4-chlorophenyl)-2-imidazoline hydrochloride (Note 1) | 0 | 40.2 |
| (Known compound) cis-2,4,5-triphenyl-2-imidazoline hydrochloride (Note 2) | 0 | 34.2 |

Note 1: Canadian Journal of Chemistry 50, 669 (1972)
Note 2: Merck Index 9, 51

EXPERIMENT 2

Effect on normalization of the number of plaque-forming cells of immunoenhancing animal Colchicine (1 mg/kg) was administered abdominally to female BALB/C mice (10 weeks old, one group: 5 mice) and, immediately thereafter, protein antigen [the bentonite particles absorbing 2,4,5-trinitrobenzene (TNP)-Keyhole Limpet Hemocyanin (KLH)] was administered abdominally to the mice (0.1 mg protein/mouse). 5 days after administration of the antigen, the mice were sacrificed under anesthesia, and the spleen cells were harvested. When the number of plaque-forming spleen cells was calculated according to the method described in. Drugs under Experimental and Clinical Research, 8(1), 5–10 (1982), this group of mice showed 129% increase in said spleen cell number as compared with a group of mice to which colchicine was not administered. On the other hand, when cis-2-(4-chlorophenyl)-4,5-diphenyl-2-imidazoline hydrochloride of the invention (Dose: 2 mg/kg) was administered orally to the mice two days before, one day before, at the day, one day after, two days after, three days after and four days after administration of the antigen, said medicated group of mice showed only 18% increase in the number of plaque-forming spleen cells as compared with a group of mice to which colchicine was not administered.

EXPERIMENT 3

Effect on normalization of the number of plaque-forming cells of immunosuppressing animal A solution containing sheep red blood cells (antigen) as a floating matter was administered abdominally to female BALB/C mice (10 weeks old, one group: 8 mice) [The number of red blood cells was about $5 \times 10^7$]. The mice were soaked in water to give restraint stress for every four hours immediately after, one day after, two days after, three days after and four days after administration of the antigen. 5 days after administration of the antigen, the mice were sacrificed under anesthesia, and the spleen cells were harvested. This group of mice showed 47% decrease in the number of plaque-forming spleen cells as compared with a group of mice which were not soaked in water. On the other hand, when cis-2-(4-chlorophenyl)-4,5-diphenyl-2-imidazoline•hydrocloride of the invention (Dose: 2 mg/kg) was administered orally to the mice two days before, one day before, at the day one day after, two days after, three days after and four days after administration of the antigen, said medicated group of mice showed only 6% decrease in the number of plaque-forming cells as compared with a group of mice which were not soaked in water.

EXAMPLE 1

14.8 ml of triethylamine are added to a mixture of 16.1 g of erythro-1,2-diamino-1,2-diphenylethane•d-iacetate, 13.7 g of 4-chlorobenziminoethyl ether•hydrochloride and 260 ml of ethanol, and the mixture is refluxed for four hours. After the reaction, the solvent is distilled off. 77 ml of a 1N aqueous sodium hydroxide solution are added to the residue, and the solution is extracted with chloroform. The extract is washed with water, dried and evaporated to remove the solvent. The residue is recrystallized from methanol to give 12.0 g of cis-2-(4-chlorophenyl)-4,5-dipheny-2-limidazoline.

Yield: 75%
M.P.: 152° to 153° C.
IR $\nu_{Max}^{Nujol}$ (cm$^{-1}$): 3200, 1619, 1595
Hydrochloride: M.P. >280° C.
Maleate: M.P. 199° to 200° C. (decomp.)
Fumalate: M.P. 233° to 235° C. (decomp.)
D,L-Lactate: M.P. 143° to 144° C. (decomp.)
L-Tartarate: M.P. 92° to 95° C. (decomp.)
Methanesulfonate: M.P. >280° C.

EXAMPLE 2

2.8 ml of triethylamine are added to a mixture of 2.9 g of erythro-1,2-diamino-1,2-diphenylethane•dihydrochloride, 1.8 g of 4-pyridyliminoethyl ether and 60 ml of ethanol, and the mixture is refluxed for two hours. After the reaction, the solvent is distilled off. 20 ml of a 10% aqueous sodium hydroxide solution are added to the residue, and the solution is extracted with chloroform. The extract is washed with water, dried and evaporated to remove the solvent. The residue is purified by silica gel column chromatography (solvent; chloroform: methanol=7:1). The product obtained above is dissolved in ethanol, and the solution is made acidic with a 10% hydrogen chloride-dioxane solution. The resulting crystals are collected by filtration to give 1.9 g of cis-2-(4-pyridyl)-4,5-diphenyl-2-imidazoline•dihydrochloride.

M.P.: >280° C.
IR $\nu_{Max}^{Nujol}$ (cm$^{-1}$): 1600, 1580

EXAMPLES 3 to 7

The corresponding erythro starting compounds (II) are treated in the same manner as described in Example 2 to give the cis imidazoline derivatives as shown in Table 2.

TABLE 2

| | Imidazole derivative (I) (hydrochloride) | | |
|---|---|---|---|
| Ex. No. | R | $X^1$ and $X^2$ | Physical properties |
| 3 | F—⌬ | H | M.P. >280° C. IR*: 1620, 1608 |
| 4 | Br—⌬ | H | M.P. >280° C. IR*: 1615, 1598 |
| 5 | Cl—⌬ (meta) | H | M.P. 251 to 253° C. IR*: 1620, 1600, 1580 |
| 6 | F—⌬ | 4-OCH$_3$— | M.P. 249 to 251° C. IR*: 1610, 1588 |
| 7 | Cl—⌬ | 4-OCH$_3$— | M.P. 280 to 283° C. IR*: 1612, 1598 |

IR* means IR $\nu_{Max}^{Nujol}$ (cm$^{-1}$) (the same in the following Table)

EXAMPLES 8 to 10

The corresponding threo starting compounds (II) are treated in the same manner as described in Example 2 to give the trans imidazoline derivatives as shown in Table 3.

TABLE 3

| | Imidazoline derivative (I) (hydrochloride) | | |
|---|---|---|---|
| Ex. No. | R | $X^1$ and $X^2$ | Physical properties |
| 8 | Cl—⌬ | 4-OCH$_3$— | M.P. 178 to 179° C. IR*: 1610 |
| 9 | Br—⌬ | 4-OCH$_3$— | M.P. 168 to 169° C. IR*: 1612 |
| 10 | Cl—⌬ | H | M.P. 281 to 284° C. IR*: 2650, 1615, 1595 |

What we claimed is:

1. An imidazoline derivative of the formula:

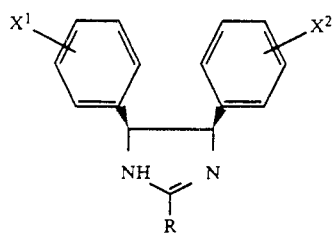

(I)

wherein R is a halogenophenyl group and $X^1$ and $X^2$ are a hydrogen atom or a pharmaceutically acceptable salt thereof.

2. cis-2-(4-chlorophenyl)4,5-diphenyl-2-imidazoline or a pharmaceutically acceptable salt thereof.

3. A pharmaceutical composition having an immunomodulating effect, which comprises as an active ingredient an effective amount of an imidazoline derivative of the formula:

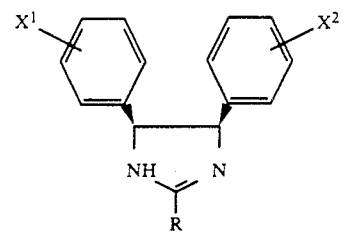

(I)

wherein R is a halogenophenyl group and $X^1$ and $X^2$ are a hydrogen atom, or a pharmaceutically acceptable salt thereof;

in admixture with a pharmaceutically acceptable carrier or diluent.

4. The pharmaceutical composition of claim 3, wherein the imidazoline derivative is cis-2-(4-chlorophenyl)-4,5-diphenyl-2-imidazoline or a pharmaceutically acceptable salt thereof.

* * * * *